(12) United States Patent
Kessler et al.

(10) Patent No.: US 9,186,470 B2
(45) Date of Patent: Nov. 17, 2015

(54) SHAPE REFLECTOR AND SURFACE CONTOUR MAPPING

(71) Applicant: Apple Inc., Cupertino, CA (US)

(72) Inventors: Patrick Kessler, San Francisco, CA (US); Nicholas Alan Rundle, San Jose, CA (US)

(73) Assignee: Apple Inc., Cupertino, CA (US)

( * ) Notice: Subject to any disclaimer, the term of this patent is extended or adjusted under 35 U.S.C. 154(b) by 97 days.

(21) Appl. No.: 13/630,025

(22) Filed: Sep. 28, 2012

(65) Prior Publication Data

US 2013/0201325 A1      Aug. 8, 2013

Related U.S. Application Data

(60) Provisional application No. 61/596,674, filed on Feb. 8, 2012.

(51) Int. Cl.
*H04N 7/18* (2006.01)
*A61M 13/00* (2006.01)
*G01B 11/25* (2006.01)

(52) U.S. Cl.
CPC .............. *A61M 13/003* (2013.01); *G01B 11/25* (2013.01)

(58) Field of Classification Search
USPC .............................................. 348/135, E7.085
See application file for complete search history.

(56) References Cited

U.S. PATENT DOCUMENTS

| | | | |
|---|---|---|---|
| 5,898,520 A * | 4/1999 | Curatu ........................ 359/465 |
| 6,416,186 B1 | 7/2002 | Nakamura | |
| 6,438,272 B1 | 8/2002 | Huang et al. | |
| 6,788,210 B1 * | 9/2004 | Huang et al. .................. 340/612 |
| 7,236,256 B2 * | 6/2007 | Yamaguchi ................... 356/603 |
| 7,433,048 B2 | 10/2008 | Park | |
| 7,463,772 B1 | 12/2008 | Lefevere et al. | |

(Continued)

FOREIGN PATENT DOCUMENTS

| | | |
|---|---|---|
| EP | 0827908 | 3/1998 |
| KR | 1020060031175 | 4/2006 |
| TW | 201105925 | 2/2011 |

OTHER PUBLICATIONS

International Search Report and Written Opinion from PCT Application No. PCT/US2013/024227, dated May 30, 2013.

(Continued)

*Primary Examiner* — Christopher S Kelley
*Assistant Examiner* — Ana Picon-Feliciano
(74) *Attorney, Agent, or Firm* — Downey Brand LLP

(57) ABSTRACT

The three dimensional surface shape of one or more layers of a reflective object is determined by examining one or more captured images reflected from the reflective object. Curved surfaces reflect a distorted image altered by the surface shape. By analyzing one or more captured images of the distorted reflected images, the shape of the surface that caused the distortion is estimated. A captured distorted image is compared to a reference undistorted image having known geometric properties. A system to capture and process such images is assembled from components including an image capture assembly such as a digital camera to capture reflected images and a positioning assembly on which to orient the components with respect to each other. Multiple surface layers of the reflective object are separately estimated using polarizations, luminance levels, chroma values or combinations thereof contained in one or more captured images.

20 Claims, 14 Drawing Sheets

(56) References Cited

U.S. PATENT DOCUMENTS

| | | | |
|---|---|---|---|
| 7,545,516 B2* | 6/2009 | Jia et al. .................. | 356/603 |
| 2002/0057438 A1* | 5/2002 | Decker .................... | 356/601 |
| 2005/0035314 A1* | 2/2005 | Yamaguchi ............ | 250/559.38 |
| 2005/0068532 A1* | 3/2005 | Qian et al. .............. | 356/369 |
| 2006/0266135 A1* | 11/2006 | Nishikawa et al. ........ | 73/866.3 |
| 2007/0280669 A1* | 12/2007 | Karim ..................... | 396/155 |
| 2008/0239316 A1* | 10/2008 | Gharib et al. ............ | 356/364 |
| 2009/0290039 A1* | 11/2009 | Kanamori et al. ........ | 348/222.1 |
| 2010/0157082 A1* | 6/2010 | Katerberg ................ | 348/222.1 |
| 2010/0214406 A1 | 8/2010 | Potapenko | |
| 2010/0283883 A1* | 11/2010 | Sato et al. ............... | 348/335 |
| 2010/0290665 A1* | 11/2010 | Sones et al. .............. | 382/100 |
| 2010/0311005 A1* | 12/2010 | Liang ....................... | 433/29 |
| 2010/0315422 A1* | 12/2010 | Andre et al. ............. | 345/426 |
| 2010/0321476 A1* | 12/2010 | Martinez et al. ......... | 348/49 |
| 2011/0050893 A1 | 3/2011 | Lee et al. | |
| 2011/0157353 A1* | 6/2011 | Takayama et al. ....... | 348/135 |
| 2011/0164114 A1* | 7/2011 | Kobayashi et al. ....... | 348/46 |
| 2012/0026085 A1 | 2/2012 | McEldowney | |

OTHER PUBLICATIONS

Taiwanese Patent Application No. 102104976—Office Action dated Dec. 22, 2014.

\* cited by examiner

SHAPE REFLECTOR AND SURFACE CONTOUR MAPPING

TECHNICAL FIELD

The present invention relates generally to the estimation of a three dimensional surface shape of an object. More particularly, methods, software, hardware, and systems are described for rapidly determining the surface profile of one or more surface layers of an object from one or more captured photographic images of a light pattern reflected from the object.

BACKGROUND

Accurately measuring the three dimensional shape of a manufactured part, such as the surface of a flat panel display, can be accomplished using an optical profilometer. The optical profilometer can measure laser generated light reflected from the surface of the manufactured part as illustrated by the prior art optical measurement system 100 in FIG. 1. A laser 102 can direct light in a narrow angle onto the surface 112 of the manufactured part under measurement test. A laser profilometer typically can measure a shape using a "main beam" of light reflected from the point "r" rather than using a "side beam" of light reflected from the point "q" and therefore a sufficiently matte, diffusely reflecting surface can be preferred. A camera 104 can be positioned to capture either the specular reflected main beam 106 or the combination of the diffuse reflected main beam 108 and the specular reflected side beam 110. A measurement process using the laser profilometer can be slow as the laser's position/orientation and/or the camera's position/orientation can be changed to measure each point reflected from the measured manufactured part. In addition, the specialized equipment to control the adjustments and measurements can be costly. To measure a reflective surface with a fine spatial resolution, tens of thousands of points can be used and can require a significant amount of time to measure a single manufactured part. Thus, there exists a need for a low cost and rapid measurement method and system to estimate the shape of one or more layers of reflective manufactured parts with a high degree of resolution and appropriate for high volume manufacturing test, assembly and quality control operations.

SUMMARY OF THE DESCRIBED EMBODIMENTS

A method for estimating a three-dimensional surface shape of two reflective surface layers of an object is described. The method is carried out by capturing by an image capture device a reflected image of the object. The reflected image of the object includes at least a first reflected image pattern and a second reflected image pattern where each reflected image pattern is reflected from a corresponding one of the two reflective surface layers. In the described embodiment, the first reflected image pattern passes through a first polarizing medium and the second reflected image pattern passes through a second polarizing medium where the first polarizing medium is characterized as having a first polarizing orientation and wherein the second polarizing medium is characterized as having a second polarizing orientation that are different from each other. The method also includes at least the steps of obtaining a first set of two-dimensional reflected image points from the first reflected image pattern, obtaining a second set of two-dimensional reflected image points from the second reflected image pattern, and generating an estimate of the three-dimensional surface shape of each of the two reflective surface layers of the object by comparing the first and second set of two-dimensional reflected image points.

In another embodiment, an apparatus is described. The apparatus includes an image capture device for capturing a first and a second reflected image pattern from the manufactured part, each reflected image pattern captured by the image capture device passing through a corresponding polarizing medium each having a different polarizing orientations, and a processing unit coupled to the image capture device and configured to process the captured reflected image patterns and to evaluate geometric properties of at least two of the multiple reflective surfaces of the manufactured part by comparing information associated with a first reflected image and a second reflected image.

In a further embodiment, a non-transitory computer readable medium for estimating a three-dimensional surface shape of at least two reflective surface layers of an object encoded as computer program code is described. The non-transitory computer readable medium includes computer program code for capturing a reflected image pattern reflected from a first reflective surface layer and a second reflective surface layer adjacent to the first reflective surface layer. In addition, the non-transitory computer readable medium includes computer program code for separating the captured reflected image pattern into a first reflected image pattern for the first reflective surface layer and a second reflected image pattern for the second reflective surface layer using a combination of luminance values and chroma values for pixels in the captured reflected image pattern. The non-transitory computer readable medium also includes computer code for computer program code for generating estimates of the three-dimensional surface shapes of the first and second reflective surface layers by comparing the first and second reflected image patterns respectively to a reference image pattern.

BRIEF DESCRIPTION OF THE DRAWINGS

The invention and the advantages thereof may best be understood by reference to the following description taken in conjunction with the accompanying drawings.

DETAILED DESCRIPTION OF EXAMPLE EMBODIMENTS

Figure 1:
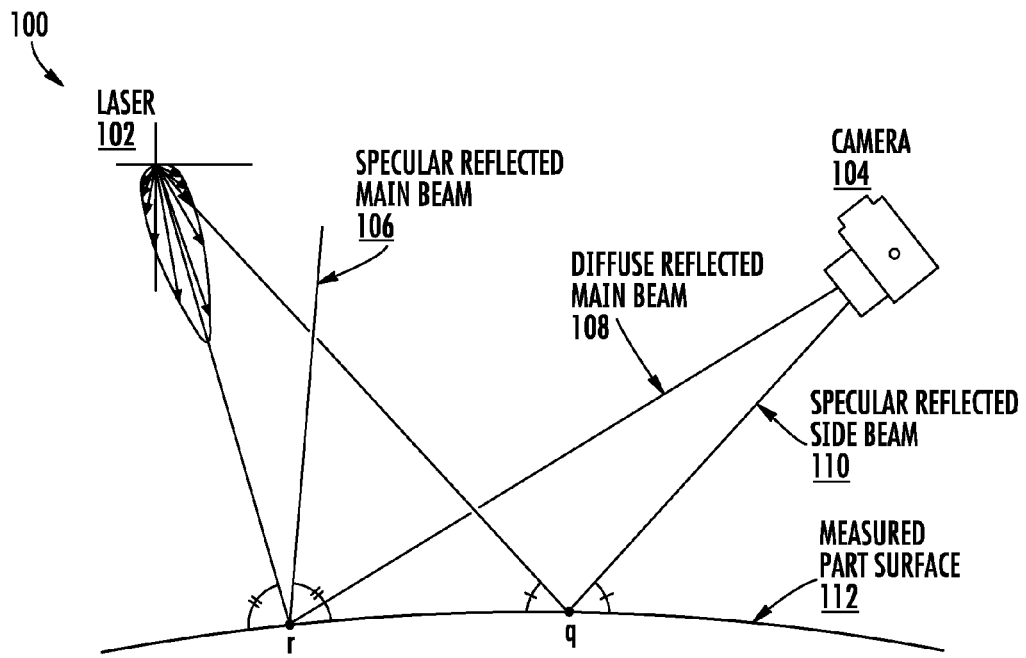
FIG. 1 illustrates a prior art optical measurement system.

The present invention relates generally to the estimation of a three dimensional surface shape of an object. More particularly, methods, software, hardware, and systems are described for rapidly determining the surface profile of one or more surface layers of an object from one or more captured photographic images of a light pattern reflected from the object.

In the following description, numerous specific details are set forth to provide a thorough understanding of the present invention. It will be apparent, however, to one skilled in the art that the present invention may be practiced without some or all of these specific details. In other instances, well known process steps have not been described in detail in order to avoid unnecessarily obscuring the present invention.

The three dimensional surface shape of a reflective object can be estimated by processing one or more captured images reflected from the reflective object. Flat specular reflective surfaces, e.g. a perfect mirror, provide an undistorted reflected image, while curved reflective surfaces produce a distorted image altered by the surface shape. Even small surface irregularities can become large distortions in the reflected image. By analyzing one or more captured images of the distorted reflection, one can estimate the three-dimensional shape of the surface that caused the distortion. A captured distorted image can be compared to a reference undistorted image for which one knows a set of geometric properties. For example, one can illuminate a predetermined patterned image onto the reflective object and compare the predetermined pattern image to a distorted version of the pattern image reflected from the reflective object. A system to capture and process such reflected, distorted images can be assembled from a number of components including a processing unit to process the images, a pattern generating assembly to transmit the image pattern onto the reflective object, a digital camera to capture the reflected image, a polarizing filter to filter the reflected image before image capture, and a positioning device on which to orient the components with respect to each other.

A system for rapidly determining geometric properties, e.g. a three-dimensional surface shape, of one or more layers of a reflective object, such as an LCD display layered together with a cover glass that includes an anti-reflective coating, is disclosed herein. An embodiment of the system can use a digital camera to capture an image pattern (e.g. an array of dots) reflected from the reflective object's surface layers. Multiple images can be captured using different reflection patterns, different light spectra, different orientations of the object and/or the digital camera, and different polarization orientations for images captured through a polarizing filter. The captured images can be processed in a processing device to calculate the shape of the reflective layers of the reflective object and generate three dimensional surface estimates and surface contour maps that illustrates surface deformations of the layers. For an image containing a number of distinguishable points, one can correlate points in the distorted reflected image to corresponding points in the original reflected image and equivalently to points on the surface of the reflective object. Using the law of reflection, one can determine an orientation of the reflective surface at the distinguishable image points that depends on the distance between the reflective surface and the digital camera. For a relatively smoothly varying surface, the three dimensional surface estimates can be constructed iteratively using estimates of the surface orientation determined at image points nearby. The surface estimate and contour map can be used by manufacturing engineers to iterate rapidly and optimize a manufacturing process through a series of measurement experiments. The system can also provide quality engineers a low cost system to inspect manufactured parts in high volume. The disclosed system and method can be substantially faster and cost less to operate than prior art laser and charge couple device systems and methods.

Figure 2:
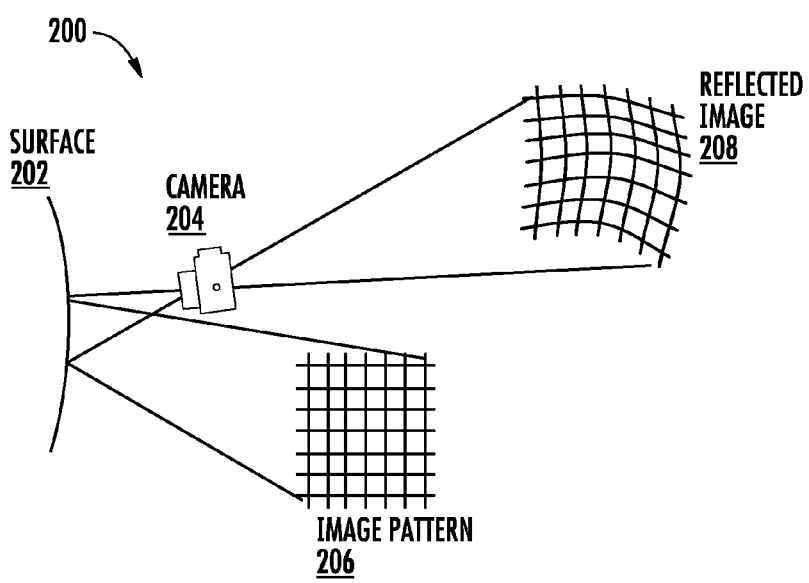
FIG. 2 illustrates distortion of a received reflected image by a curved reflective surface.

FIG. 2 illustrates distortion 200 of image pattern 206 captured by a camera 204 after reflection from a reflective surface 202. The captured reflected image 208 shows a distorted version of the image pattern 206. The distortions in the reflected image can be correlated to the shape of the reflective surface 202. Specular reflected images can reveal surface irregularities more readily than an image projected onto a diffuse reflective surface, as differences in surface orientation between adjacent points on the surface are magnified in the reflected image as the distance between the camera 204 and the reflective surface 202 increases. The captured two dimensional reflected image 208 can be used to estimate the three dimensional shape of the reflective surface 202. When the surface 202 includes multiple adjacent reflective layers, the reflected image 208 can include a superposition of reflected images, one from each of the different reflective layers. In representative embodiments, the images for each of the reflected images can be separated using light properties, such as luminance levels, chroma values and/or light polarizations, as described further herein.

Figure 3A:
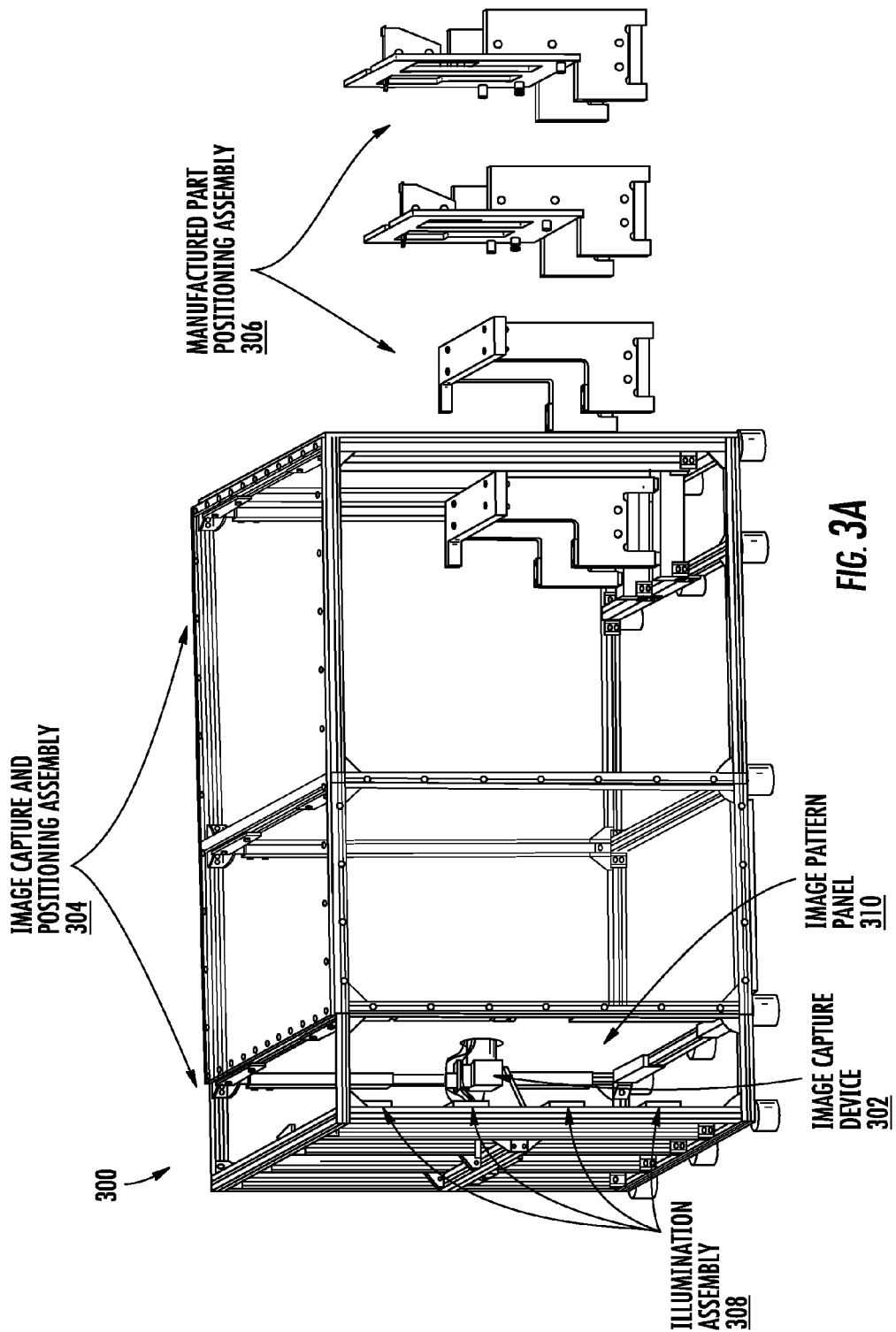
FIG. 3A illustrates a system for image capture and positioning to measure a reflective surface shape of a manufactured part.

FIG. 3A illustrates an embodiment of a system 300 for capturing one or more images reflected from one or more reflective surface layers of a manufactured part. The system 300 includes an image capture and positioning assembly 304 on which various components of the system 300 can be mounted and positioned. A manufactured part (not shown) can be mounted in a positioning assembly 306 that can be placed in the image capture and positioning assembly 304. An image pattern can be illuminated onto the manufactured part by illuminating an image pattern panel 310 using lights mounted in an illumination assembly 308. The image pattern panel 310 can be larger than the manufactured part under test and can accommodate a wide variety of manufactured parts. The image pattern on the image pattern panel can include a sufficiently large number of distinct points to provide a high resolution for measuring the three-dimensional geometric shape of the manufactured part. An image capture device 302 (e.g. a digital camera) can be mounted to capture a reflection from the reflective surfaces of the manufactured part. An opening in the image pattern panel 310 can provide a portal through which the image capture device 302 can capture the reflected image pattern. The image capture device 302, the image pattern panel 310 and the manufactured part can be oriented spatially with respect to each other by the positioning assembly 304/306. In a representative embodiment, the image capture device 302 can be adjusted to face the reflective manufactured part to capture the reflected image. Depending on the size and shape of the reflective manufactured part, the lens attached to the image capture device 302 can be chosen to capture a preferred portion of the reflected image. Rather than only adjusting the lens of the image capture device 302 to change the field of view, the image capture and positioning assembly 304 can also be adjustable allowing for different distances between the reflective manufactured part mounted in the manufactured part positioning assembly 306 and the image capture device 302. The image pattern on the reflective manufactured part can include multiple light and dark regions so that reflected light regions can be captured by the image capture device 302. A preferred embodiment of the invention can use an array of light dots arranged in a regular grid on a dark background. Other pattern images can also be used. In a preferred embodiment, an image sensor in the image capture device 302, the image pattern panel 310 and the manufactured part mounted in the manufactured part positioning assembly 306 can be approximately co-planar, which can simplify calculations for processing the captured reflected images to determine the three-dimensional surfaces of the manufactured part.

Figure 3B:
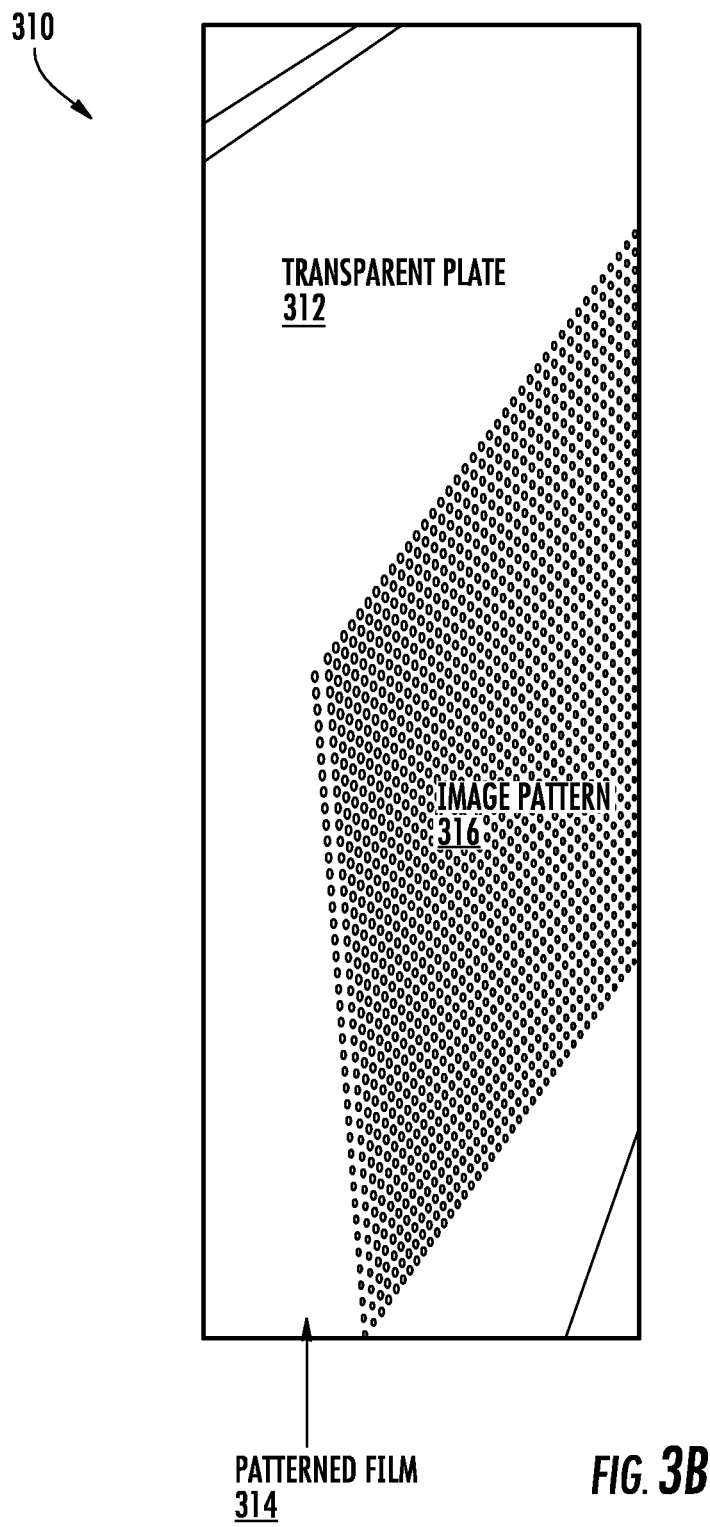
FIG. 3B illustrates an image pattern generating plate.

FIG. 3B illustrates an image pattern panel 310 that can be placed in front of a light source to produce an image pattern on the reflective manufactured part. The image pattern panel 310 can include a transparent plate 312, e.g. a transparent acrylic panel, on which can be mounted a patterned film 314 containing opaque regions and transparent areas that can form an image pattern 316. Different image patterns 316 can be created by using different patterned films 314. Alternatively, an image pattern panel 310 can be created using any combination of opaque and transparent regions, such as through a metal plate or opaque plastic panel drilled with holes. The image pattern panel 310 illustrated FIG. 3B is advantageously light in weight, easy to assemble and can offer different image patterns by substituting films having different image patterns. With bright light sources mounted in the illumination assembly 308 behind the image pattern panel 310, an image pattern 316 can be produced having a high ratio of signal (high luminance dot region) to noise (low luminance background region). With "high SNR" images, the method described herein can provide accurate results including surfaces with anti-reflective coatings that can decrease the luminance levels of images reflected from the surface of the manufactured part under test.

Figure 3C:
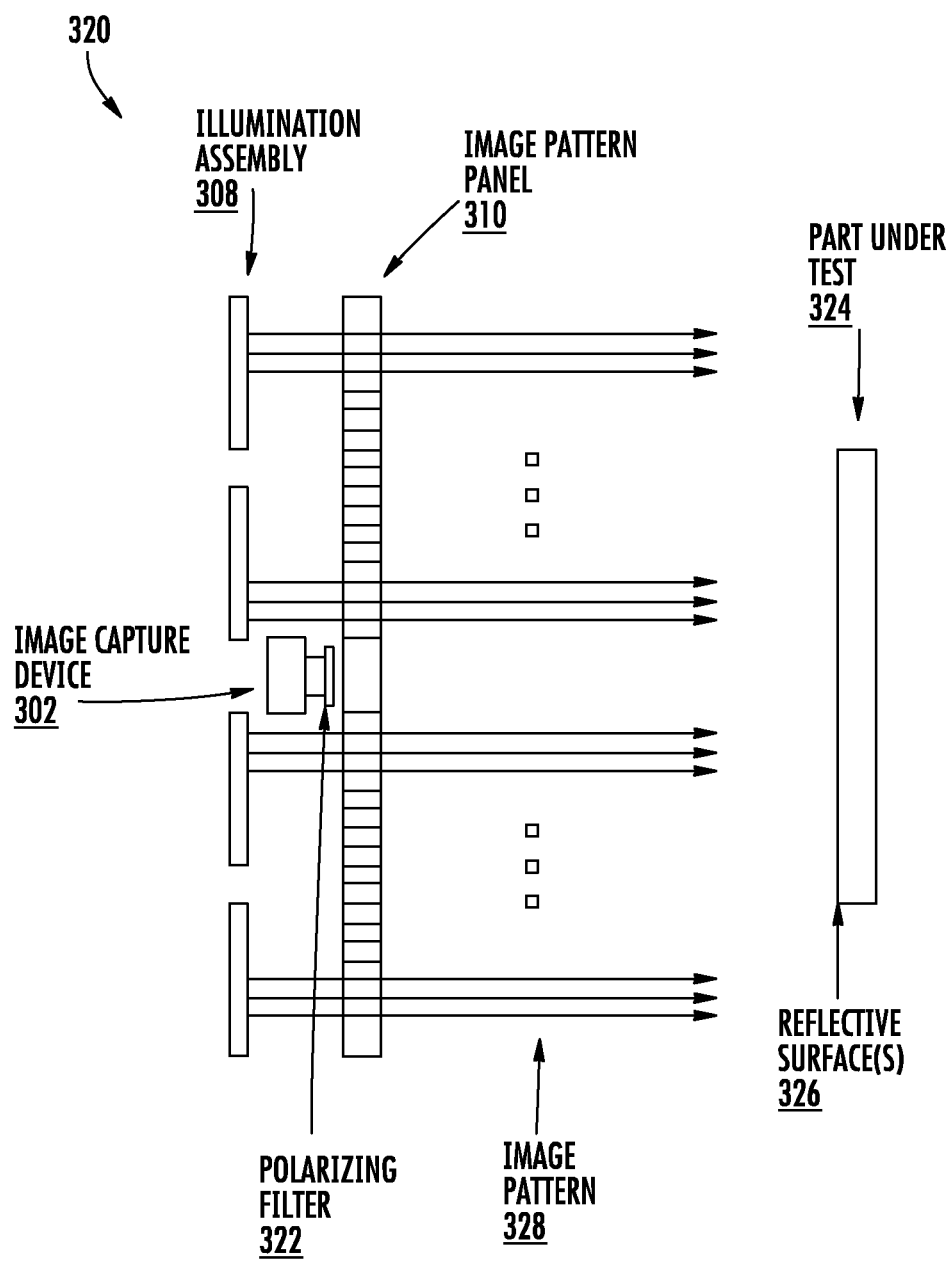
FIG. 3C illustrates select elements of a cross-section of the image capture and positioning assembly of FIG. 3A.

FIG. 3C illustrates a cross section 320 of select components of the image capture and positioning system 300 shown in FIG. 3A. The illumination assembly 308 can include a set of light panels, such as LED light panels or fluorescent lights, mounted behind the image capture device 302. The image pattern panel 310 can "filter" light emanating from the illumination assembly 308 creating an image pattern 328 onto reflective surface(s) 326 of a manufactured part 324 under test. In a representative embodiment, the image pattern 328 can include multiple circular dots having an approximately uniform shape and light value (luminance/chroma). The uniformity of shape and color for the components of the projected image pattern 328 can aid in the processing of captured reflected images. Reflections from the reflective surface(s) 326 can be captured by the image capture device 302. A polarizing filter mounted on the image capture device can be rotated to different positions to filter the received reflected images in order to discriminate between reflected images having different polarizations. In an embodiment, one of the reflective surfaces 326 of the manufactured part 324 can reflect the image pattern 328 with a polarization, while a second reflective surface 326 can reflect the image pattern 328 without a polarization. Using different polarizations for the polarizing filter 322, the image capture device 302 can capture an image that includes a combination of reflected image patterns from the two reflective surfaces or only one reflected image pattern from one of the surfaces (e.g. the polarized reflected image pattern can be filtered out by the polarizing filter 322 in front of the image capture device 302 before the image is captured).

Figure 4:
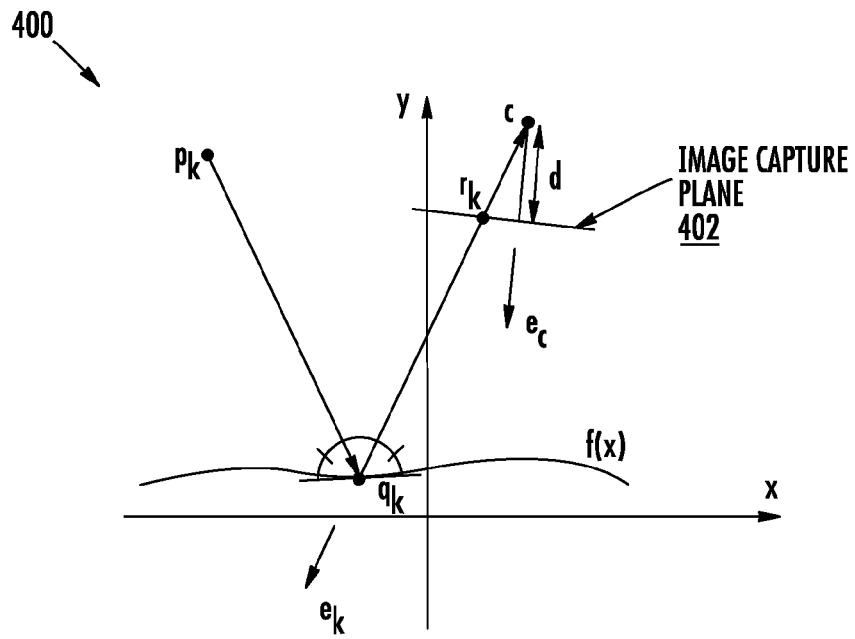
FIG. 4 illustrates a two-dimensional mathematical model for measurement of a reflection.

FIG. 4 illustrates a light ray originating from a point $p_k$ (which can represent a transparent dot of the image pattern 328) and travelling toward a reflective surface depicted as curve f(x). (Vectors are denoted by bold face herein.) The light ray can reflect from a point $q_k$ on the curve f(x), where the angle of incidence of the light ray can equal the angle of reflection with respect to a tangent of the curve f(x) at $q_k$. The light ray can pass through a point $r_k$ of an image capture plane 402 in a camera 204 (image capture device 302) positioned at point c. The camera 204 can be pointed in a direction defined by a unit vector $e_c$ perpendicular to the image capture plane 402. The reflected light ray can travel from the point $q_k$ to the point c along a direction $-e_k$. (Note that the unit vectors $e_c$ and $e_k$ in general can be coincident.) In one embodiment, multiple points $p_1, p_2, \ldots, p_N$ arranged in a line can be projected on the curve f(x) resulting in a set of points $r_1, r_2, \ldots, r_N$ received on the image plane. The curve f(x) can be reconstructed using the set of received points $r_1, r_2, \ldots, r_N$ using knowledge of the transmitted points $p_1, p_2, \ldots, p_N$.

The distance d between the image capture plane 402 and the camera position c can be determined by comparing an actual distance of a reference feature on an object to a dimension in a captured image of the reference feature. In one embodiment, the reference feature can be a pair of distinguishable marks scribed on a part of the image capture and positioning assembly 304 or on the manufactured part positioning assembly 306 or on the manufactured part (not shown). In another embodiment, the reference feature can be a pair of distinguishable marks projected onto a reference flat object positioned in the manufactured part positioning assembly 306. For an actual distance B between the two distinguishable marks on the object and a measured distance D from the reference feature to the camera position c, the distance d=(bD)/B. Calibration of the system shown in FIG. 3A can adjusting the camera to position one or more reference marks on the positioning assembly (or on a reference object placed in the positioning assembly) to preferred locations in a viewed camera image, e.g. in an optical viewfinder or on an electronic display. Calibration can also include determining the distance d between the camera position c and the image plane. In the system 300 illustrated in FIG. 3A, the image capture device 302, the image pattern panel 310 and the manufactured part under test mounted in the manufacture part positioning assembly 306 can be approximately co-planar, thereby simplifying the calibration process.

In general, a set of image points $\{p_k\}$ can result in a set of captured points $\{r_k\}$ on the image capture plane 402. Portions of the function f(x) (or more generally a three dimensional surface) that curve inward (concave) can cause adjacent image points in the set of image points $\{p_k\}$ to converge in a captured image, while portions that curve outward (convex) can cause adjacent image points to diverge. For a region R of a surface that reflects a pattern P into the camera, let g(P) denote the captured image pattern. To determine the shape of the surface region R, the mapping g(•) can be an injective function, i.e. g(•) can be a function (cannot map one point $p_k$ to multiple image points $r_k$) and g(•) can be one-to-one (cannot map two different points $p_k$ to a single image point $r_k$). If each image point $r_k$ can be linked to a unique source point $p_k$ (e.g. by using different colored source points, or by flashing the source points on/off at different times) then the shape of the region R can be uniquely determined. The shape of region R can also be determined by iteratively constructing a surface estimate starting from one or more distinct image points as outlined further herein.

Figure 5A:
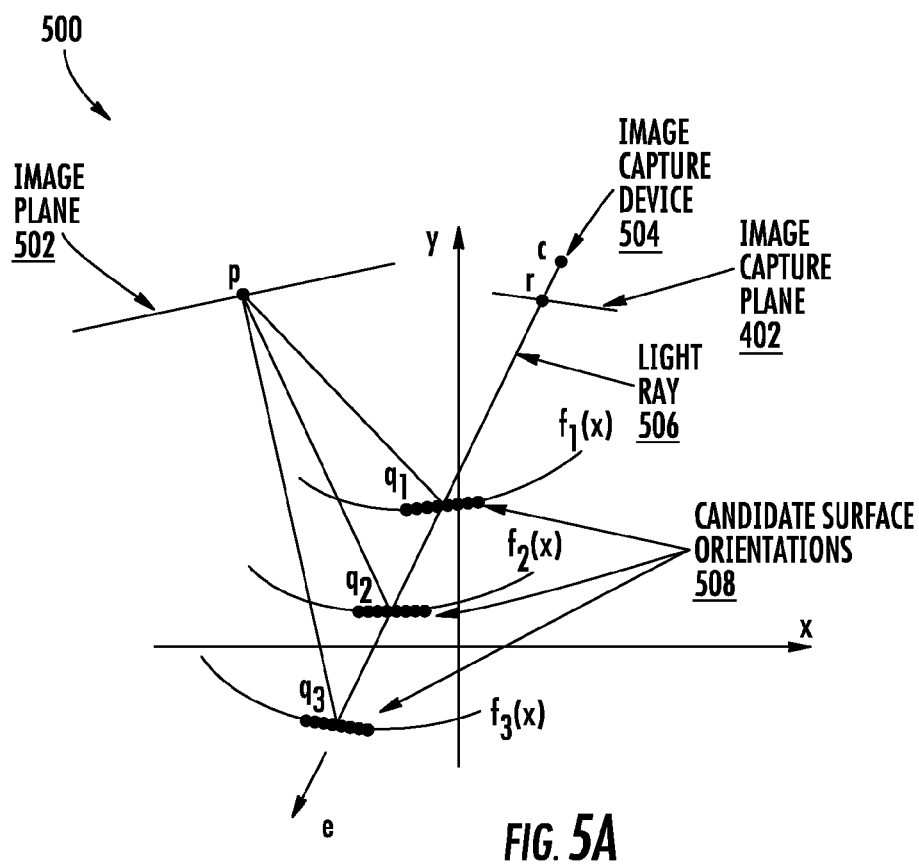
FIG. 5A illustrates multiple candidate reflective surface orientations for a fixed image capture position.
Figure 5B:
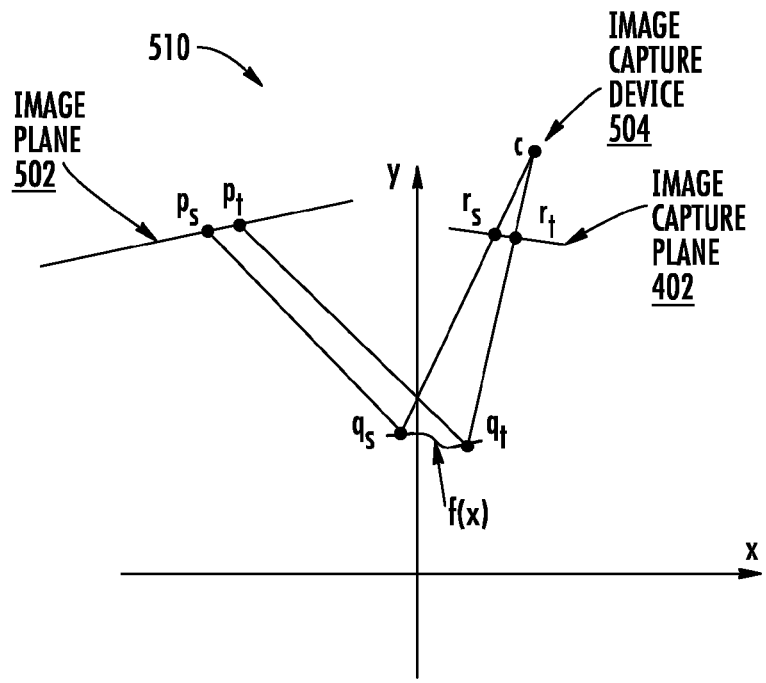
FIG. 5B illustrates connecting two neighboring points on a reflective surface estimate.

As shown in FIG. 5A, each ray of light entering an image capture device 504 along a light ray 506 and originating from a point p on an image plane 502 can be reflected by any of a plurality of candidate surfaces 508 having different positions and orientations. A single point r in a captured image can result from light reflected from the curve $f_1(x)$ at point $q_1$, or from curve $f_2(x)$ at point $q_2$, or from curve $f_3(x)$ at point $q_3$. As the angle of incidence must equal the angle of reflection at any reflective point, one can determine candidate surface orientations 508 at each possible intersecting reflective point along the direction −e into the image capture device 504. (The unit vector e in FIG. 5A corresponds to the unit vector $e_k$ in FIG. 4.) For a light ray that originates at the point p on the image plane 502 and a function f(x) that crosses the light ray 506 at a distance/away from the image capture device 504 at position c, a unit tangential t and a unit normal n to the surface f(x) at a reflection point q is given by Equation (1)

$$t = -\frac{u+e}{\|u+e\|}, \quad (1)$$
$$n = \frac{u-e}{\|u-e\|},$$

where the reflection point q=c+le, and u is defined as the unit vector in the direction p−q. Each point r in a captured image can result from any of a plurality of surfaces, each positioned at a different distance from the image capture device 402 positioned at position c. To resolve this ambiguity, one can use information about the surface orientation determined for points in the captured image near the point r. As shown in FIG. 5B, starting with a first received image point $r_s$, for which one has determined a surface orientation that can occur at a corresponding reflection point $q_s$, one can determine a function f(x) that connects the reflection point $q_s$ to a reflection point $q_t$ that corresponds to a neighboring adjacent point $r_t$ in the captured image. Obviously numerous different functions can connect two points. In a preferred embodiment, one can use a smooth function that is tangential to the surface at each reflection point and has minimum curvature in between as will be detailed next.

Figure 6:
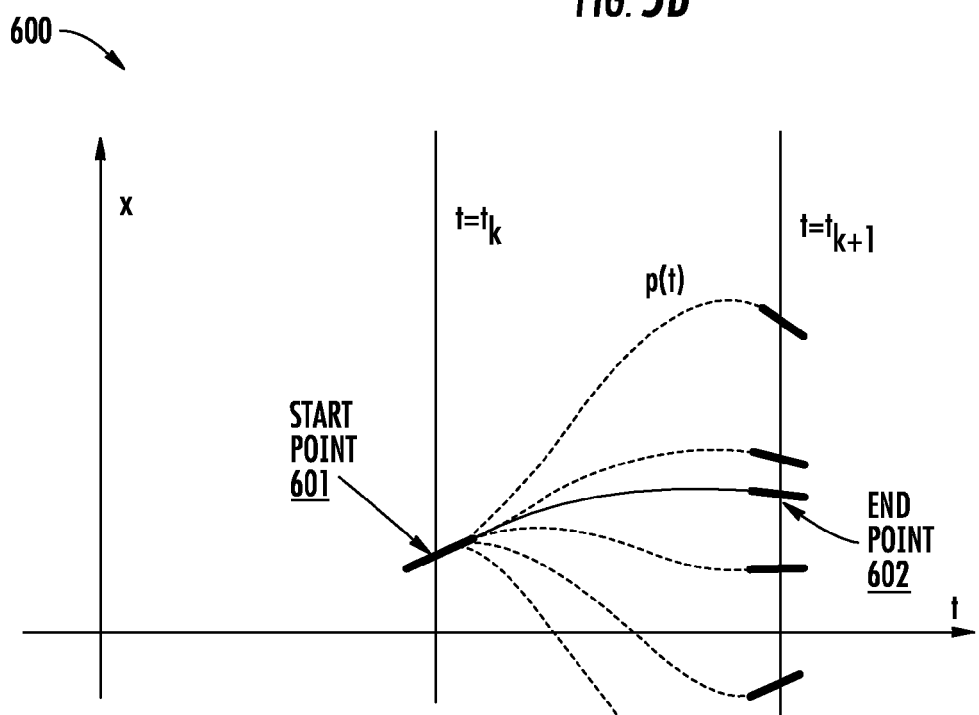
FIG. 6 illustrates connecting multiple candidate reflective surface orientations to a known start point surface.

FIG. 6 illustrates a first reflection point (start point 601 at $t=t_k$) having a known surface orientation that can connect to any one of a plurality of second reflection points (at $t=t_{k+1}$), each with a different surface orientation. The path p(t) that connects the two reflection points is tangential to the corresponding surface orientations at those reflection points, i.e. at $t=t_k$ and $t=t_{k+1}$. In one embodiment, p(t) is chosen to be a cubic polynomial function that connects the two reflection points. In a preferred embodiment, the path p(t) is chosen to minimize a curvature function ($C^2 = \ddot{x}_k^2 + \ddot{x}_{k+1}^2$). In FIG. 6, the cubic polynomial path p(t) with minimum curvature is shown connecting the start point 601 to an end point 602. To determine which end point 602 results in the path p(t) with minimum C, we can iteratively solve for a value of $x_{k+1} = \gamma$. For each γ, the cubic polynomial path p(t) between $t_k$ and $t_{k+1}$ that has the correct slope at both the start point 601 ($t=t_k$) and at an end point ($t=t_{k+1}$) can be given by Equation (2)

$$p(t) = x_k a(t) + \dot{x}_k \alpha(t) + \gamma b(t) + g(\gamma)\beta(t) \quad (2)$$

where $g(\gamma) = f(\gamma, t_{k+1})$, and where the basis polynomials a(t), b(t), α(t), and β(t) can be given by Equations (3), (4), (5) and (6)

$$a(t) = \frac{2}{d^3}(t-d/2)^3 - \frac{3}{2d}(t-d/2) + \frac{1}{2} \quad (3)$$

$$\alpha(t) = \frac{t}{d^2}(t-d)^2 \quad (4)$$

$$b(t) = \frac{2}{d^3}(d/2-t)^3 - \frac{3}{2d}(d/2-t) + \frac{1}{2} \quad (5)$$

$$\beta(t) = \frac{t^2}{d^2}(t-d) \quad (6)$$

where $d=t_{k+1}-t_k$. The curvature function C is the 2-norm of $u=a+\gamma b + g(\gamma)c$ where $$a = x_k \frac{6}{d^2}\begin{bmatrix}-1\\1\end{bmatrix} + \dot{x}_k \frac{2}{d}\begin{bmatrix}-2\\1\end{bmatrix} \quad (7)$$

$$b = \frac{6}{d^2}\begin{bmatrix}1\\-1\end{bmatrix} \quad (8)$$

$$c = \frac{2}{d}\begin{bmatrix}-1\\2\end{bmatrix} \quad (9)$$

The nonlinearity of the function g(γ) is usually weak, and so an iteration as defined in Equation (10)

$$\gamma_{i+1} = \gamma_i - \frac{\langle (a+g(\gamma_i)c), b\rangle}{\langle b, b\rangle} \quad (10)$$

can converge to a value for $x_{k+1}$ to within a preferred level of numerical precision within a few steps. Herein the notation $\langle a, b\rangle$ denotes a dot product between vectors a and b. By choosing a smooth, cubic polynomial path p(t) with least curvature, one minimizes changes in slope between the start point and the end point where one lacks information.

Figure 7:
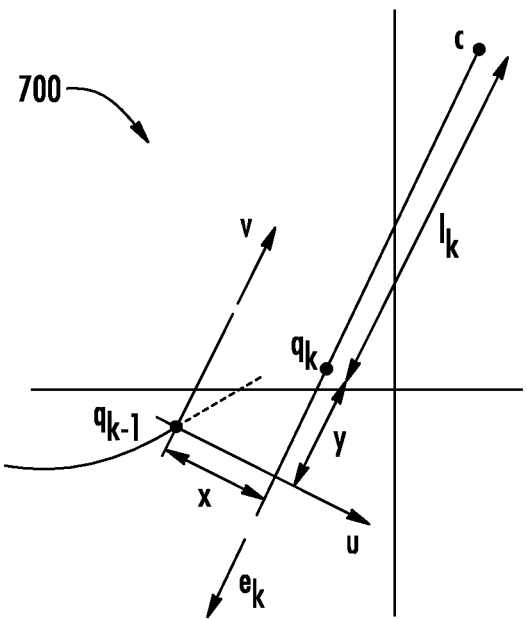
FIGS. 7 and 8 illustrate additional mathematical models for measurement of a reflection.

FIG. 7 applies the idea discussed above with respect to FIG. 6 to extending a curve that can start at point $q_{k-1}$ and can end at a point $q_k$. For a light ray entering a camera situated at point c along a direction $-e_k$, one can determine a slope for each possible reflection point that can occur along the light ray. Suppose we have determined the point $q_{k-1}$ (and necessarily the slope at $q_{k-1}$), and we want to find the point $q_k = c + l_k e_k$ along the light ray (i.e. determine the distance $l_k$ between the reflection point $q_k$ and the camera point c). Consider the unit vectors u and v defined to be perpendicular to and tangential to the light ray into the camera point c respectively. In particular let $v = -e_k$ and $u = Re_k$, where $$R = \begin{bmatrix} 0 & -1 \\ 1 & 0 \end{bmatrix}$$

is a 90 degree counter clockwise rotation matrix. Using the rotated (u, v) coordinate system let x be the distance in the u direction and y be the distance in the v direction from the point $q_{k-1}$ to the point $q_k$. Because the distance $l_k$ can be given by $l_k = \langle e_k, q_{k-1} - c \rangle - y$, one can determine $l_k$ by solving for the distance y. Solving for the point $q_k$ is the same as described for determining the position of the end point 602 in FIG. 6 (where the rotated axes u and v in FIG. 7 correspond to the axes t and x in FIG. 6 respectively). A normal vector n perpendicular to curves that cross the light ray at different values of y can be determined using Equation (1). The corresponding slope of the curve at the point $q_k$ in the rotated coordinate frame can be determined by Equation (11)

$$\frac{dy}{dx} = -\frac{\langle n, u \rangle}{\langle n, v \rangle}. \tag{11}$$

The values of the distance y and the slope $$\frac{dy}{dx}$$

in Equation (11) correspond to the values $\gamma$ and $g(\gamma)$ used for the iteration of Equation (10). Thus we can use the iterative method described above to determine a solution for the point $q_k$.

Figure 8:
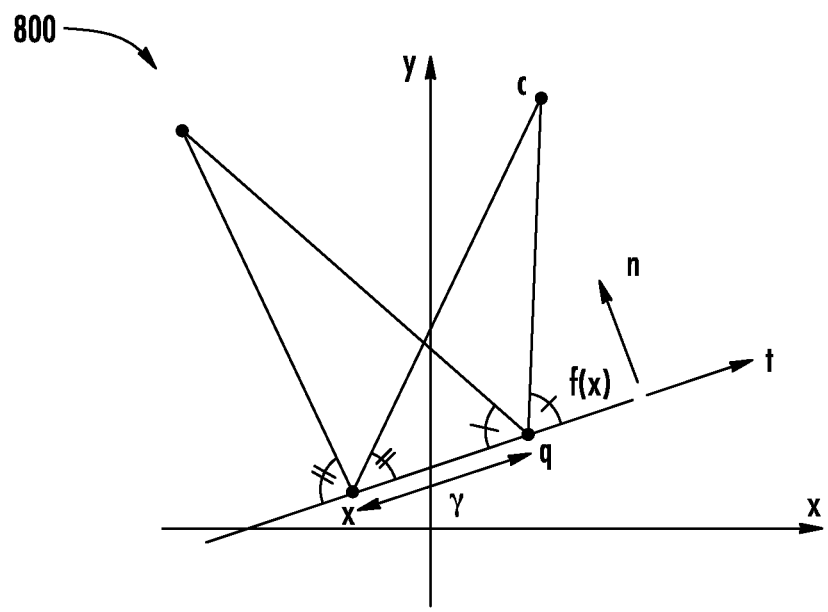

Accuracy of the method described above for determining an estimate of a point on a surface can be checked by simulating an image capture. In the simplest case, consider a reflective surface f(x) that is a line as shown in FIG. 8. Define n and t to be the unit normal and unit tangential vectors to the line f(x) respectively, and let x be a point on the line that is not necessarily the reflection point. (Note that the angle of incidence and the angle of reflection are shown as unequal at the point x and equal at the reflection point q.) The reflection point $q = x + \gamma t$ on the line f(x) for light originating from a point p can be given by Equation (12).

$$\gamma = \frac{\langle n, c-x \rangle \langle t, p-x \rangle + \langle n, p-x \rangle \langle t, c-x \rangle}{\langle n, c-x \rangle + \langle n, p-x \rangle} \tag{12}$$

If the reflective surface f(x) is a curve instead of a line, then one can iterate a sequence of points $x_i$ such that the reflection point $$q = \begin{bmatrix} \tilde{x} \\ f(\tilde{x}) \end{bmatrix}$$

is defined by a limit $\tilde{x}$ of the sequence of points $x_i$. Given a reflective surface f(x) and a set of points $p_k$, with these constructions one can generate each of the resulting image points $r_k$ captured on the image plane of the camera situated at point c. Thus one can simulate capturing an image of a reflection. To test the accuracy of the surface estimation method described above, one can start with a known reflective surface f(x), use ray tracing to compute a set of points of a simulated captured image, construct an estimate of the reflective surface g(x) from the simulated captured image, and compute a error difference f(x)−g(x) between the original reflective surface f(x) and the constructed reflective surface g(x).

Figure 9:
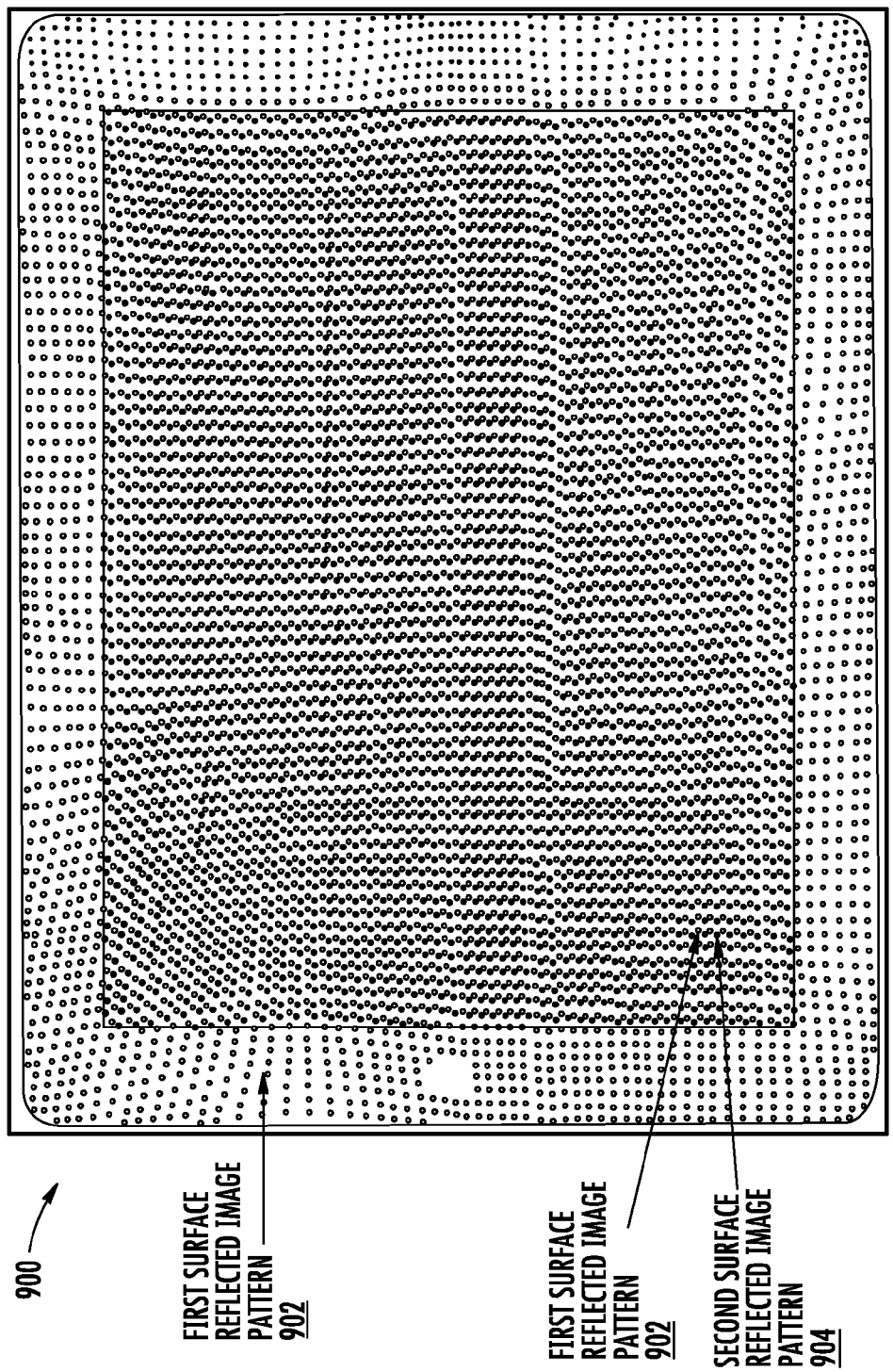
FIG. 9 illustrates an image capture of two superimposed reflections from two adjacent surfaces of a manufactured part.

FIG. 9 illustrates an image capture 900 of two superimposed reflected image patterns captured from two different adjacent reflective surface layers of a manufactured part. The manufactured part can include a first reflective surface, e.g. a protective cover glass mounted on top of an LCD display for a "tablet computer" and a second reflective surface, e.g. the LCD display, adjacent to the first reflective surface. The first reflective surface can produce a first surface reflected image pattern 902, while the second reflective surface can produce a second surface reflected image pattern 904. In a representative manufactured part as illustrated in FIG. 9, the first reflective surface can substantially cover an entire surface of the manufactured part, while the second reflective surface can cover a smaller portion of the surface of the manufactured part beneath the first reflective surface. In areas of the manufactured part that include both first and second reflective surfaces, two different reflected image patterns 902/904 can result, while in regions having only the first reflective surface, only the first surface reflected image pattern 902 can result as illustrated in FIG. 9. Each of the two reflective surfaces can have a different three-dimensional shape, and the first surface reflected image pattern 902 and the second surface reflected image pattern 904 can be non-overlapping, at least across certain areas of the manufactured part. Two reflected image patterns 902/904 (e.g. two sets of dots) can be captured by the image capture device 302, e.g. one image pattern 902 reflected from the protective cover glass and one image pattern 904 reflected from the LCD display.

Figure 10:
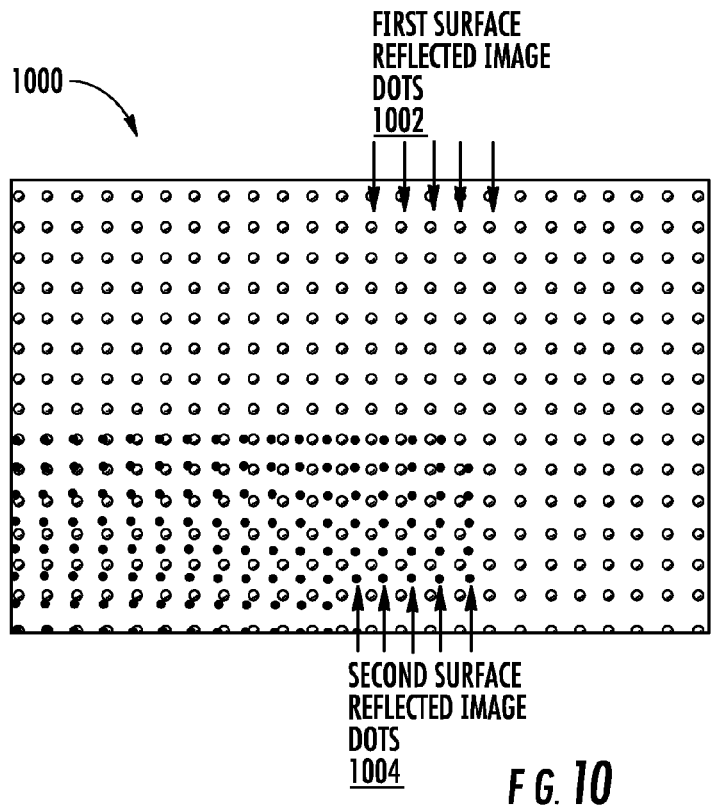
FIG. 10 illustrates an enlarged section of the image capture of FIG. 9.

Each of the adjacent reflective surfaces can modify the image pattern differently, including directionality due to the individual three dimensional shape of the reflective surface, light intensity and light chroma values due to the presence/absence and amount of anti-reflective coatings applied to the reflective surface, and light polarization due to properties of the reflective surface. FIG. 10 illustrates an enlarged section 1000 of the image capture 900 of FIG. 9. At the periphery of the manufactured part the image pattern reflects from the first reflective surface resulting in a first set of "first surface" reflected image dots 1002 having a position, light intensity and light chroma value that differ from a second set of "second surface" reflected image dots 1004 reflected in the center section of the manufactured part. An anti-reflective coating on the first reflective surface can attenuate light intensity (luminance levels) of the reflected dots as well as filter select light frequencies resulting in differently colored reflected dots. The second reflective surface, e.g. on an LCD display, can reflect a wider range of light frequencies resulting in a brighter (higher luminance value) reflected image dot 1004 from the second surface than resulting from a reflected image dot 1002 from the first reflective surface that includes an anti-reflective coating. The second surface reflected image dots 1004 can appear "whiter" than the "colored" first surface reflected image dots 1002.

Figure 11:
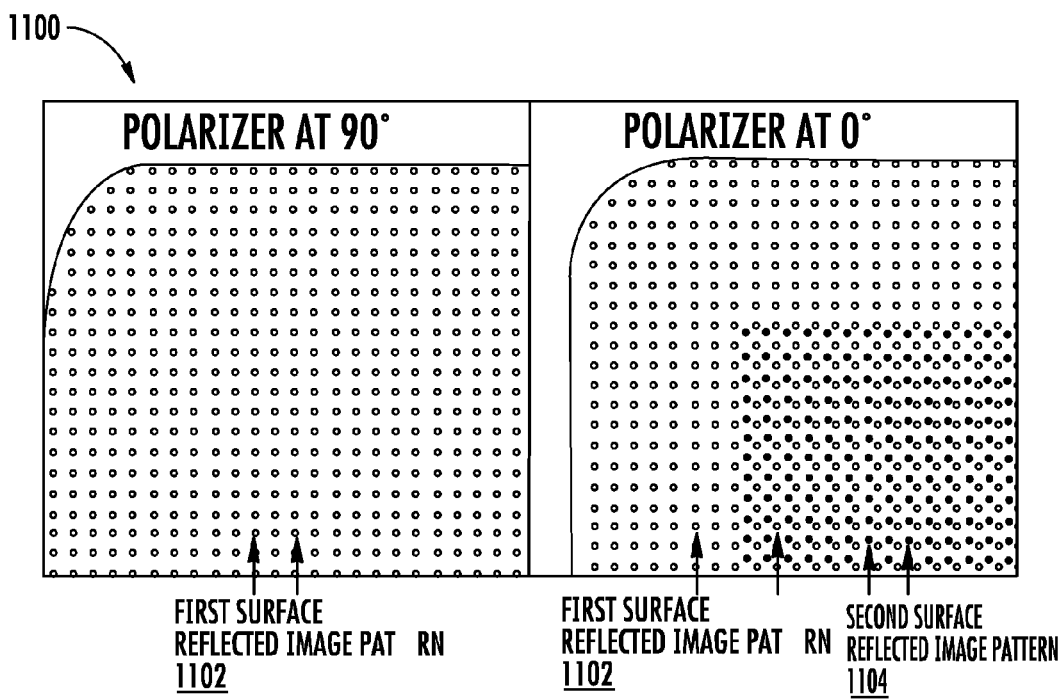
FIG. 11 illustrates two image captures for two adjacent surfaces through a polarizing filter with different polarization orientations.

In a representative embodiment, the second reflective surface can polarize light reflected from its surface resulting in a reflected image pattern composed of reflected image dots having a particular polarization. Depending on the orientation of the polarizing filter 322 through which the reflected image pattern can pass to be captured by the image capture device 302, the polarized reflected image pattern can be captured or can be filtered out as shown in FIG. 11. In a representative embodiment, for the polarizing filter 322 oriented in a first position (e.g. at a nominal 0 degrees), reflected image patterns from both the first reflective surface and the second reflective surface can pass through the polarizing filter 322 and be captured by the image capture device 302. With the polarizing filter 322 oriented in a second position (e.g. at a nominal 90 degrees), the non-polarized reflected image pattern from the first reflective surface can pass through the polarizing filter 322, while the polarized reflected image pattern from the second reflective surface can be blocked by the polarizing filter 322. As illustrated in FIG. 11, an image capture for one position of the polarizing filter 322 can include only the first surface reflected image pattern 1102, while an image capture for a second position of the polarizing filter 322 can include both the first surface reflected image pattern 1102 superimposed with the second surface reflected image pattern 1104. The polarizing filter 322 can conveniently separate polarized reflected image patterns from non-polarized reflected image patterns. A processing unit can combine the information from the two image captures to produce an image pattern for each of the separate reflective surfaces, from which separate three-dimensional surface estimates for the two separate reflective surfaces can be constructed. In one embodiment, the luminance values for a first reflected image pattern can differ substantially from the luminance values for a second reflected image pattern (e.g. the reflected image pattern from the reflective surface having an anti-reflective coating can have a lower luminance value). The processing unit can separate the image patterns based on measured luminance values (e.g. by threshold levels) and/or using measured chroma values (different colors) in addition to or separately from using the polarizing filter 322 to generate separate images. The measured chroma and luminance values for the reflected image pattern from the reflective surface that includes the anti-reflective coating can also be used to measure variance in the anti-reflective coating across the reflective surface that includes the anti-reflective coating.

Figure 12:
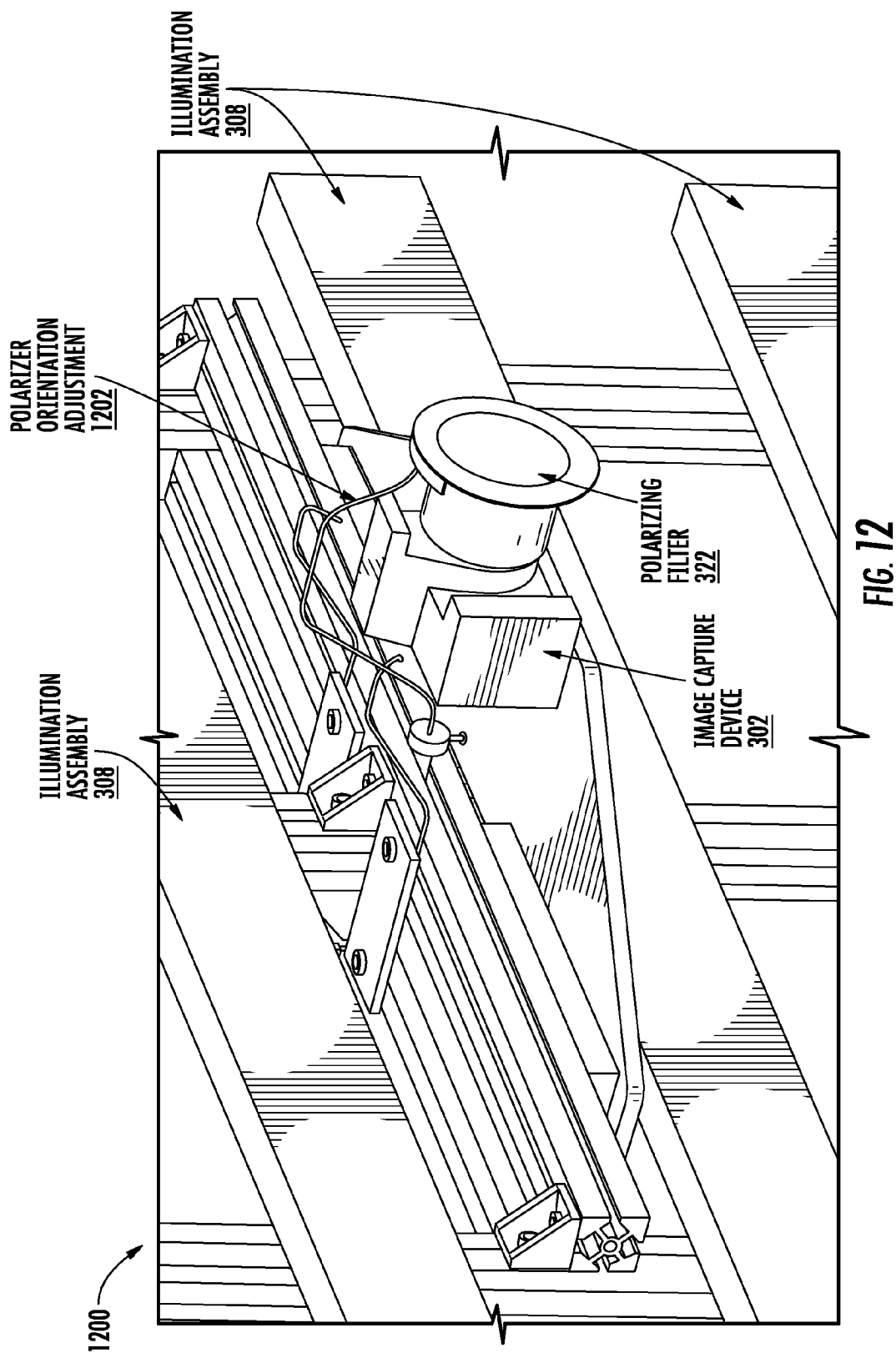
FIG. 12 illustrates elements of the image capture and positioning system of FIG. 3A.

FIG. 12 illustrates elements of the image capture and positioning system 300 illustrated in FIG. 3A. As shown, the image capture device 302 can include the polarizing filter 322 mounted in front of a lens connected to a polarizer orientation adjustment 1202 mechanism. The illumination assembly 308 can be positioned around and/or behind the image capture device to illuminate the image pattern panel to send the image pattern to the manufactured part.

As described above, a three dimensional surface of a reflective object can be estimated using a two-dimensional image capture of an image reflection. The image can include a regular pattern, such as an array of dots. Locations of the dots can be determined by processing the captured image. Each image dot can correspond to a cluster of pixels (pixilated reflected dot) in a digital captured image. Note that for the purpose of locating the dots, the captured image can be reduced to a monochrome image, which can be derived from one or more color (red, green, blue) channels in the captured color image generated by the image capture device 302. In a digital still camera having a Bayer array of pixels, the green channel can provide the most information and thus can be preferred. (Alternatively, luminance values that combine information from all pixels can also be used.) Using an array of numbers, each number representing a value for the green channel in a captured image, we can create a smoothed image by low pass filtering each pixel. For example, we can average the values for each pixel using the values of its surrounding (nearest neighbor) pixels. Each value for a pixel in the filtered image can be converted to a binary value (i.e. black or white only) depending upon a threshold resulting in a binary pixilated reflected dot. The low pass filtering (smoothing) operation can ensure that dots do not split into multiple pixel clusters after the threshold operation. Alternatively one can exclude the low pass filtering operation and directly generate a binary pixilated image from the captured monochrome image (possibly resulting in multiple distinct "white" pixels for each pixel cluster corresponding to a single reflected dot). The resulting binary pixilated image can be transformed by expanding each "white" pixel into a 3×3 (or some other pattern) of "white" pixels, thereby "dilating" each pixel into a larger cluster of pixels. Using either method, the resulting binary pixilated image preferably contains a distinct, undivided cluster of "white" pixels corresponding to each captured reflected dot.

A two dimensional geometric location for each dot can be determined from the binary pixilated image as the centroid of each cluster of "white" pixels. One method to identify all pixels in each cluster can be to assign an integer to each "white" pixel in the image. This can be done by working through the image pixels one by one. If a new pixel is white, and has no neighboring pixels that are white, the pixel can be assigned a new integer. If the new white pixel has neighboring white pixels that are already labeled, the new pixel can be assigned the minimum of the integers assigned to its labeled white neighbors. After a first pass, some of the pixels in the same cluster can have been assigned different integers, but this multiple assignment can be fixed by a second pass. Having identified the pixels comprising each cluster, the centroids of the pixel clusters can be computed. Next, one can determine the generating dot corresponding to each pixel cluster centroid. This correspondence can be determined by branching out from one or more reference dots, which can be identified (before monochrome and binary conversion) uniquely based on a different captured color from the remaining dots in the image (e.g. the reference dots can be colored blue instead of white). A neighboring centroid can be connected to an existing identified centroid by searching in an annular region defined (when possible) along the direction of branches already established. Using the calculated centroids and the relationship among them, one can estimate the surface shape of a reflective object that "distorts" the image pattern as described above.

Accuracy of the surface shape estimate can depend on the spacing between dots in the image pattern. More closely spaced dots can provide more information about the surface shape; however, the curvature of the surface across some areas of the reflective object can cause adjacent image dots in the image to be very close together in the reflected image. Accuracy in certain regions of the surface can be improved by changing the density of the dot grid (or the size of each dot) to ensure distinguishable (but still closely spaced) dots. In addition one can also change the position of the image capture device or the orientation of the reflective object to provide a different angle of view. One can also change the magnification of the field of view by altering the focal length of the camera lens to capture a specific region of the specular reflective object. A composite estimate of the specular reflective surface can then be assembled from multiple images captured using different image patterns, different spatial orientations, or different fields of view or any combination thereof.

Figure 13:
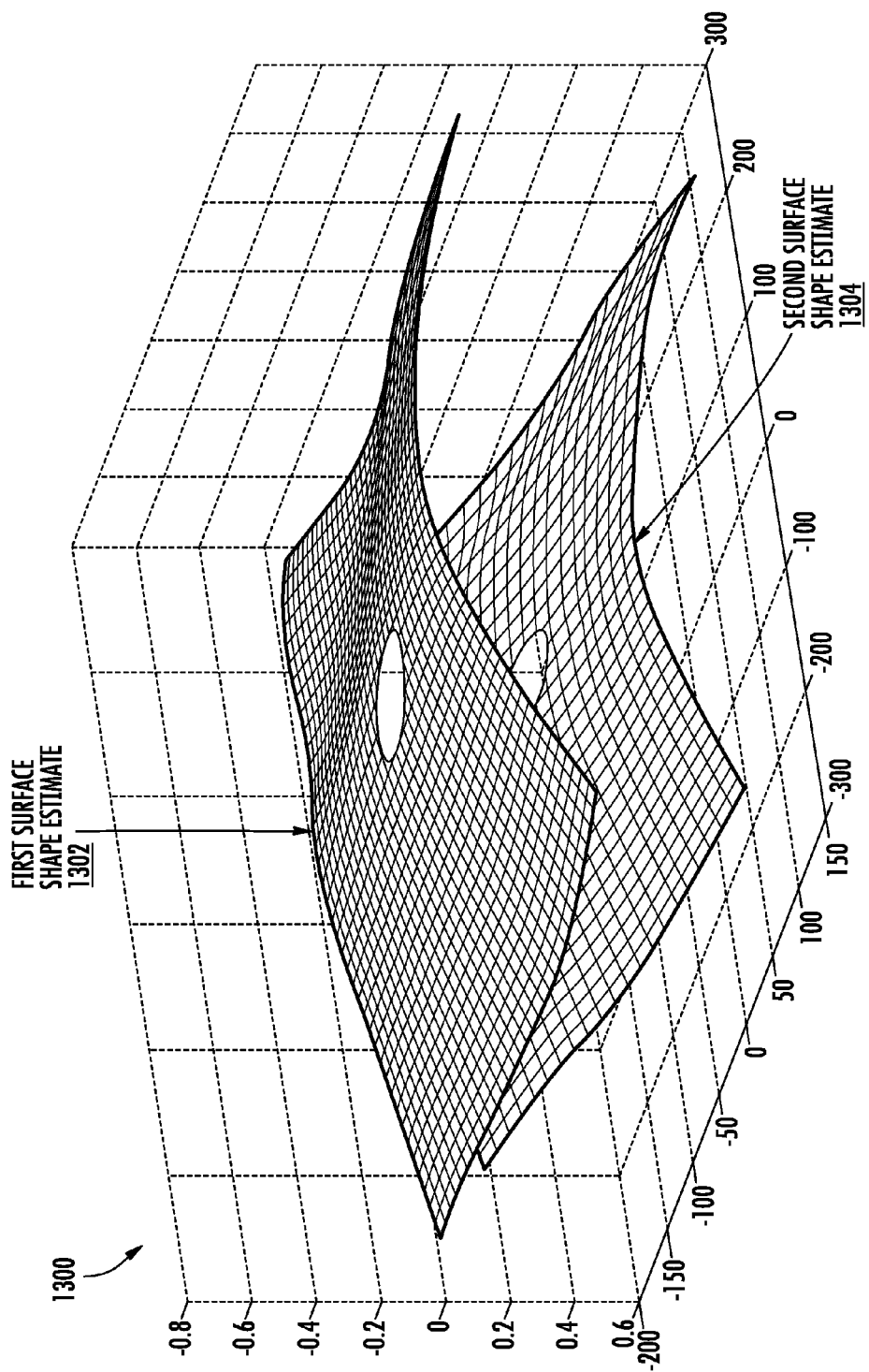
FIG. 13 illustrates two three-dimensional surface estimates for two adjacent surfaces of a manufactured part generated from image captures of reflected image patterns.

FIG. 13 illustrates two three-dimensional surface estimates for two adjacent reflective surfaces based on image captures of a manufactured part as described above. Both an estimate of the three-dimensional surface shape of an outermost layer of the manufactured part, i.e. a first surface shape estimate 1302, and an estimate of the three-dimensional surface shape of an inner layer adjacent to the outermost layer, i.e. a second surface shape estimate 1304, can be generated from one or more image captures using the image capture and positioning system 300 illustrated in FIG. 3A and described above. A high level of resolution of the geometric shape of the reflective surfaces can be achieved using a fine grid of image points, e.g. more than 15,000 points used in the representative surface shape estimates 1302/1304 illustrated in FIG. 13. The image capture and processing by a processing unit can be accomplished in seconds rather than minutes/hours than can be required to capture a comparable number of points using a mechanical or laser optical measurement system. In a representative embodiment, the first surface shape estimate 1302 can correspond to a shape for a protective cover glass surface while the second surface shape estimate 1304 can correspond to a shape for an LCD display surface mounted beneath the protective cover glass surface.

In a representative embodiment, the three-dimensional surface shape estimates can be compared to image captures of light leakages that can occur in an LCD display surface when the LCD display surface varies from a flat surface and allows light from a backlight to "leak" through. A uniform "black level" can be preferred when the LCD display is "on", and the three-dimensional mechanical shape of the LCD display can be altered during a manufacturing process, e.g. mounting the LCD display in a housing of a manufactured part. One or more three-dimensional surface shape estimates can be used to refine the manufacturing process by correlating a three-dimensional surface shape with a high degree of spatial accuracy to quality levels required to achieve a property of the LCD display, such as limiting light leakage that can affect background black levels of the LCD display. With a rapid image capture and processing system, one or more pass/fail criteria can be developed for factory test that can improve quality of the manufactured parts ensuring manufactured parts can achieve uniform geometric properties within specified tolerances.

In some embodiments, light sources mounted in the illumination assembly 308 can include different types of light having different spectral properties, e.g. infrared or ultraviolet light to "see" through coatings or layers of one or more reflective surfaces of the manufactured part. Similarly different filters in place of or in addition to the polarizing filter 322 can be used to alter the captured images by filtering the light before capture. Different processing algorithms of the captured images can also be used to separate superimposed image patterns received from multiple reflective layers of a manufactured part. The projected image pattern can also be "pre-warped" to a "non-uniform pattern" to account for a non-flat reflective surface on a manufactured part. Different positions and/or orientations of the manufactured part while under test can also be used to separate reflected image patterns from different reflective surfaces captured together in one or more images. A co-planar system as described herein can be more robust and simpler to calibration and implement in a manufacturing process.

Figure 14:
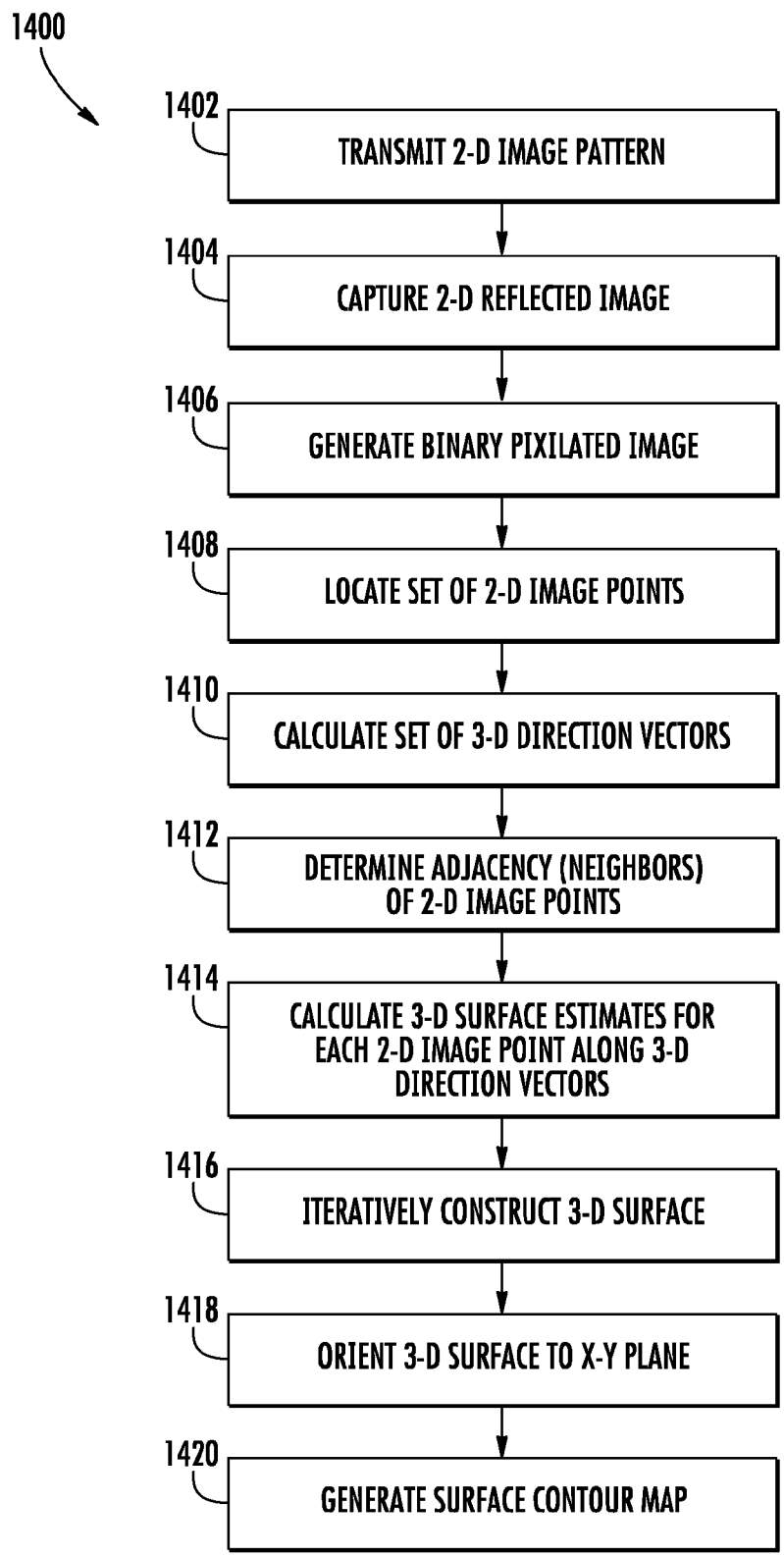
FIG. 14 outlines a representative method to generate a surface estimate of a reflective object.

FIG. 14 outlines a method 1400 to estimate a reflective surface shape of an object. In step 1402 an image pattern generating device (such as a fluorescent light) can transmit a two-dimensional image pattern toward a reflective object having one or more reflective surfaces. The image pattern can be a regular array of dots or other shapes with distinctly identifiable points. Preferably the image uses an array of light and dark regions with sharp edges. For example an image can include a plurality of light dots separated on a dark background, each dot being distinctly identifiable. Many different image patterns can be used by the method described herein, and the method is not limited to the exemplary image pattern described.

In step 1404 an image capture device captures a two-dimensional image of a reflection of the image pattern. In one embodiment, the image capture device is a digital still camera that can generate a digital pixilated image. The reflected image can contain one or more superimposed distorted versions of the image pattern, wherein the distortions can be caused by variations in the shape of the reflective surfaces of a reflective object, e.g. a manufactured part having a layered reflective surface. In step 1406 a binary pixilated image can be generated from the captured pixilated two-dimensional reflected image. Preferably the binary pixilated image includes an array of pixel clusters, each pixel cluster corresponding to an individual identifiable point in the received reflected image. In step 1408 a set of two-dimensional image points can be identified and located using the binary pixilated image. Preferably each pixel cluster in the binary pixilated image generates a unique two-dimensional image point. In a preferred embodiment, the two-dimensional image point is a centroid of the pixel cluster.

In step 1410, a set of three-dimensional direction vectors are calculated, one for each two-dimensional image point. Each three-dimensional vector can represent the direction that a light ray travels from a reflection point on the surface of the specular reflective object to the image plane of the image capture device for a respective two-dimensional image point. In step 1412 adjacency information can be determined for each of the two-dimensional image points relating each point to its neighboring points. In step 1414 a set of three-dimensional surface estimates can be calculated for each two-dimensional image point along its corresponding three-dimensional direction vector. Each element of the set of three-dimensional surface estimates can represent a different position and orientation of the reflective object's surface from which the two-dimensional image point can be reflected into the image capture device. In step 1416 a three-dimensional surface estimate of the reflective object can be iteratively constructed starting with one or more reference points of the surface. For each three-dimensional surface estimate, an element of a set of three-dimensional surface estimates for a two-dimensional image point can be chosen that minimizes a curvature function of a curve connecting the three-dimensional surface estimate to a previously estimated three dimensional surface estimate. In a preferred embodiment the curve includes a cubic polynomial function. In step 1418 the three-dimensional surface estimate can be oriented with respect to a reference plane. In step 1420 a surface contour map can be generated from the oriented three-dimensional surface estimate.

Figure 15:
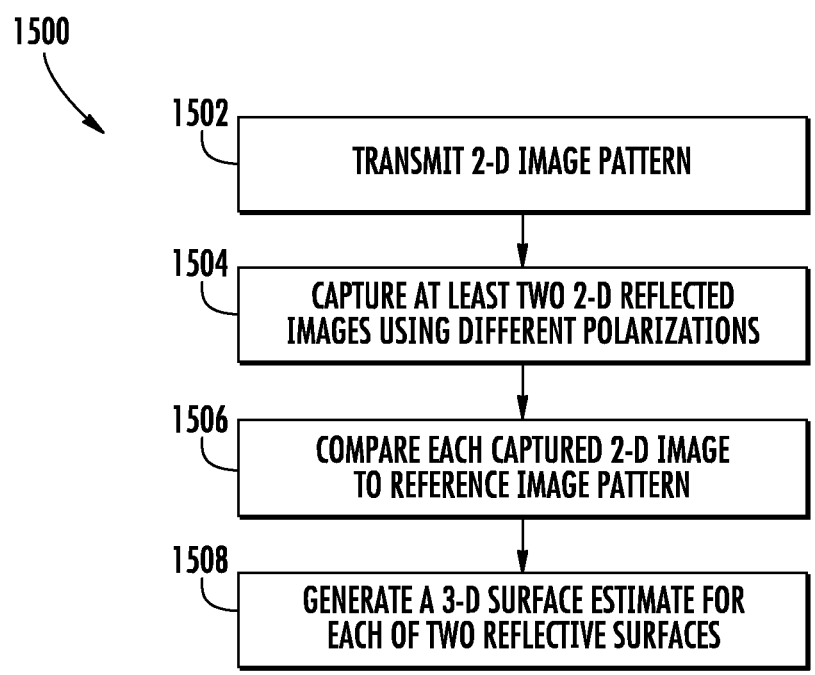
FIG. 15 outlines a representative method to generate surface estimates for two adjacent surfaces using image captures through a polarizing filter.

FIG. 15 illustrates another representative method 1500 for generating three-dimensional surface estimates for two reflective surfaces of a manufactured part. In step 1502, a two-dimensional image pattern is projected onto the manufactured part. In step 1504, at least two different two-dimensional reflected images are captured by an image capture device. Each of the two different two-dimensional reflected images can be captured using a different polarization position for a polarizing filter placed in front of the image capture device. In step 1506, the two different two-dimensional reflected images are compared to a reference image pattern to determine a variation of surface shape from a pre-determined three-dimensional surface shape. In step 1508, a three-dimensional surface estimate is generated for each of two different adjacent reflective surfaces in the manufactured part. In a representative embodiment, one of the reflective surfaces reflects the two-dimensional image pattern with a polarization. In the representative embodiment, one of the two-dimensional reflected images are captured with the polarizing filter positioned to block the polarized reflected two-dimensional image pattern from the one of the reflective surfaces. In the representative embodiment, the other of two different adjacent reflective surfaces does not induce a polarization to the reflected two-dimensional image.

Figure 16:
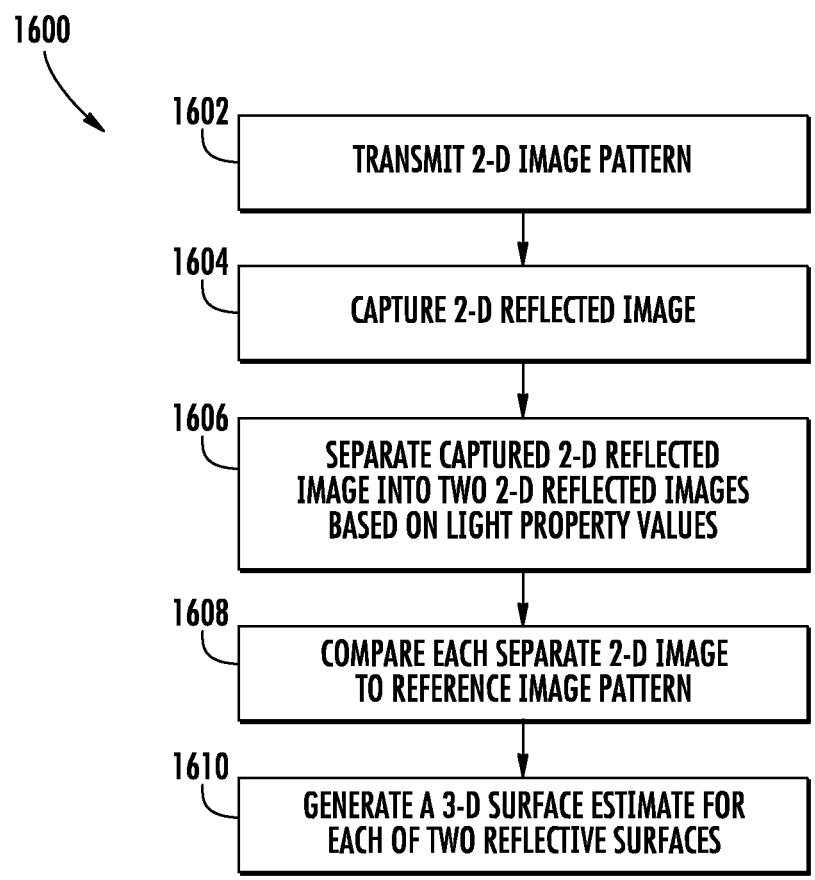
FIG. 16 outlines a representative method to generate surface estimates for two adjacent surfaces using a single image capture.

FIG. 16 illustrates another representative method to generate three-dimensional surface estimates for two adjacent reflective surfaces of a manufactured part. In step 1602, a two-dimensional image pattern is projected onto the manufactured part. In step 1604, a two-dimensional reflected image is captured that includes reflected image patterns from each of the two adjacent reflective surfaces. The captured two-dimensional image pattern includes two superimposed image patterns, one reflected from each of two different adjacent reflective surfaces. In step 1606, the captured two-dimensional reflected image is separated to two different reflected images based on light property values. The two-dimensional image pattern is processed to separate the two-dimensional image pattern into separate image patterns, one for each of the two different adjacent reflective surfaces. In a representative embodiment, the processing includes separation based on luminance values and/or chroma values. In a representative embodiment, a threshold for a luminance value is used to separate the two image patterns. In step 1608, the two separate two-dimensional images are compared to a reference image pattern. In step 1610, two different three-dimensional surface estimates, one for each of the two different adjacent reflective surfaces, are generated using the two separated image patterns.

Various aspects of the described embodiments can be implemented by software, hardware or a combination of hardware and software. The described embodiments can also be encoded as computer program code on a non-transitory computer readable medium. The non-transitory computer readable medium is any data storage device that can store data which can thereafter be read by a computer system. Examples of the non-transitory computer readable medium include read-only memory, random-access memory, CD-ROMs, DVDs, magnetic tape and optical data storage devices. The computer program code can also be distributed over network-coupled computer systems so that the computer program code is stored and executed in a distributed fashion.

The various aspects, embodiments, implementations or features of the described embodiments can be used separately or in any combination. The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

The advantages of the embodiments described are numerous. Different aspects, embodiments or implementations can yield one or more of the following advantages. Many features and advantages of the present embodiments are apparent from the written description and, thus, it is intended by the appended claims to cover all such features and advantages of the invention. Further, since numerous modifications and changes will readily occur to those skilled in the art, the embodiments should not be limited to the exact construction and operation as illustrated and described. Hence, all suitable modifications and equivalents can be resorted to as falling within the scope of the invention.

What is claimed is:

1. A method for estimating a three-dimensional surface shape of two reflective surface layers of an object, the method comprising:
    capturing, by an image capture device and when a polarizing filter is blocking a first reflected image pattern reflected from a first reflective surface of the object, a second reflected image pattern reflected from a second reflective surface of the object;
    capturing, by the image capture device and when the polarizing filter is blocking the second reflected image pattern, the first reflected image pattern, wherein the first reflected image pattern exhibits a different amount of luminance than the second reflected image pattern as a result of a difference between the first reflective surface and the second reflective surface;
    obtaining a first and second set of two-dimensional reflected image points from the first reflected image pattern and the second reflected image pattern respectively;
    calculating a set of three-dimensional direction vectors for the first set and second set of two-dimensional reflected image points;
    calculating a set of three-dimensional surface estimates for each two-dimensional image point along its corresponding three-dimensional direction vector, wherein each element of the set of three-dimensional surface estimates represents a different position of a surface of the object; and
    minimizing a curvature function of a curve connecting an estimate of the three-dimensional surface to a previously generated three-dimensional surface estimate.

2. The method as recited in claim 1, wherein the first and second reflected image patterns each include information related to a shape of the two reflective surface layers of the object.

3. The method as recited in claim 1, wherein the curve corresponds to a cubic polynomial function.

4. An apparatus for estimating a three-dimensional surface shape of a manufactured part having multiple reflective surfaces, the apparatus comprising:
    a polarizing filter;
    an image capture device configured to:
        capture, when the polarizing filter is blocking a first reflected image pattern reflected from a first reflective surface of the manufactured part, a second reflected image pattern reflected from a second reflective surface of the manufactured part, and
        capture, when the polarizing filter is blocking the second reflected image pattern, the first reflected image pattern, wherein the first reflected image pattern exhibits a different amount of luminance than the second reflected image pattern as a result of a difference between the first reflective surface and the second reflective surface; and
    a processing unit coupled to the image capture device and configured to:
        generate a first and second set of two-dimensional reflected image points from the first reflected image pattern and the second reflected image pattern respectively;
        calculate a set of three-dimensional direction vectors for each two-dimensional image point;
        calculate a set of three-dimensional surface estimates for each two-dimensional image point along its corresponding three-dimensional direction vector; and
        minimize a curvature function of a curve connecting an estimate of the three-dimensional surface to a previously generated three-dimensional surface estimate.

5. A machine-readable non-transitory storage medium storing instructions that, when executed by a processor included in a computing device, cause the computing device to carry out steps that include:

capturing, by an image capture device and when a polarizing filter is blocking a first reflected image pattern reflected from a first reflective surface of an object, a second reflected image pattern reflected from a second reflective surface of the object;

capturing, by the image capture device and when the polarizing filter is blocking the second reflected image pattern, the first reflected image pattern, wherein the first reflected image pattern exhibits a different amount of luminance than the second reflected image pattern as a result of a difference between the first reflective surface and the second reflective surface;

generating a first and second set of two-dimensional reflected image points from the first reflected image pattern and the second reflected image pattern respectively;

calculating a set of three-dimensional direction vectors for each two-dimensional image point;

calculating a set of three-dimensional surface estimates for each two-dimensional image point along its corresponding three-dimensional direction vector, wherein each element of the set of three-dimensional surface estimates represents a different position and orientation of a surface of the object; and minimizing a curvature function of a curve connecting an estimate of the three-dimensional surface to a previously estimated three-dimensional surface estimate.

6. A system for estimating a three-dimensional surface shape of two reflective surface layers of an object, the system comprising:

a polarizing filter;

an image capture device configured to:

capture, when the polarizing filter is blocking a first reflected image pattern reflected from a first reflective su4rface of the object, a second reflected image pattern reflected from a second reflective surface of the object, and capture, when the polarizing filter is blocking the second reflected image pattern, the first reflected image pattern, wherein the first reflected image pattern exhibits a different amount of luminance than the second reflected image pattern as a result of a difference between the first reflective surface and the second reflective surface;

an image pixelator configured to generate first and second set of two-dimensional reflected image points from the first reflected image pattern and the second reflected image pattern; and a processing unit configured to:

determine adjacency information for each two-dimensional image point, the adjacency information relating each two-dimensional image point to a neighboring point, calculate a three-dimensional direction for each two-dimensional image points, calculate an estimate of the three-dimensional surface of each of the first and second reflective surfaces of the object based on the two-dimensional image points, and minimize a curvature function of a curve connecting the estimate of the three-dimensional surface to a previously estimated three-dimensional surface estimate.

7. The system as recited in claim 6, wherein the curve includes a cubic polynomial function.

8. The method as recited in claim 1, wherein the polarizing filter is capable of passing a non-polarized first reflected image and blocking a polarized second reflected image.

9. The method as recited in claim 1, further comprising:
rotating the polarizing filter to a different position in order to discriminate between polarizations of the first reflected image pattern and the second reflected image pattern.

10. The method as recited in claim 1, further comprising:
rotating the polarizing filter after the image capture device captures the first reflected image pattern.

11. The system as recited in claim 6, wherein the polarizing filter is configured to rotate at a time between the image capture device capturing the first reflected image pattern and the second reflected image pattern.

12. The method of claim 1, wherein each of the first and second reflected image patterns include multiple circular dots.

13. The method of claim 12, wherein the multiple circular dots have approximately uniform shape and luminance values.

14. The method of claim 1, wherein obtaining a first and second set of two-dimensional reflected image points includes pixelating the first and second reflected image patterns after one or more image patterns are blocked by the polarizing filter.

15. The method of claim 1, further comprising:
determining a distance between the image capture device and the object.

16. The method of claim 1, wherein the first reflected image pattern corresponds to a first luminance value that is different than a second luminance value corresponding to the second reflected image pattern.

17. The method of claim 1, wherein the first reflected image pattern includes a first color that is different than a second color included in the second reflected image pattern.

18. The machine-readable non-transitory storage medium of claim 5, wherein the steps further include:
generating a surface contour map from the estimate of the three-dimensional surface.

19. The system of claim 6, wherein the polarizing filter is mounted to the image capture device.

20. The system of claim 6, wherein the image pixelator is configured to pixelate the first and second reflected image patterns after one or more image patterns are blocked by the polarizing filter.

* * * * *